US009243300B2

(12) United States Patent
Nakano et al.

(10) Patent No.: US 9,243,300 B2
(45) Date of Patent: Jan. 26, 2016

(54) LACTIC ACID BACTERIUM FOR INHIBITING PRODUCTION OF GASTRIC ACID AND GASTRIN

(75) Inventors: Yasuhiro Nakano, Isehara (JP); Yuji Aiba, Hadano (JP); Michihiko Kumagai, Yokohama (JP); Fumiya Asukabe, Tokyo (JP); Yasuhiro Koga, Isehara (JP)

(73) Assignee: SNOWDEN KABUSHIKIKAISHA, Tokyo (JP)

( * ) Notice: Subject to any disclaimer, the term of this patent is extended or adjusted under 35 U.S.C. 154(b) by 417 days.

(21) Appl. No.: 13/337,544

(22) Filed: Dec. 27, 2011

(65) Prior Publication Data

US 2012/0177606 A1 Jul. 12, 2012

(30) Foreign Application Priority Data

Jan. 7, 2011 (JP) .................................. 2011-013451

(51) Int. Cl.
| A61K 35/747 | (2015.01) |
| C12R 1/225 | (2006.01) |
| A23C 9/123 | (2006.01) |
| A23C 19/06 | (2006.01) |

(52) U.S. Cl.
CPC ............... *C12R 1/225* (2013.01); *A23C 9/1234* (2013.01); *A23C 19/062* (2013.01); *A61K 35/747* (2013.01); *A23Y 2220/43* (2013.01)

(58) Field of Classification Search
CPC ............... A23C 19/062; A23C 9/1234; A23Y 2220/43; C12R 1/225
USPC ............................................. 424/93.4, 93.45
See application file for complete search history.

(56) References Cited

FOREIGN PATENT DOCUMENTS

| JP | 08-268899 A | 10/1996 |
| JP | 2002-515458 A | 5/2002 |
| JP | 2002-537336 A | 11/2002 |
| JP | 2005-539013 A | 12/2005 |
| JP | 2008-169198 A | 7/2008 |
| JP | 2008-189572 A | 8/2008 |
| JP | 4457364 B2 | 11/2008 |
| WO | WO-95/18110 A1 | 7/1995 |
| WO | WO-99/59631 A1 | 11/1999 |
| WO | WO-00/50037 A1 | 8/2000 |
| WO | WO-2004/012659 A2 | 2/2004 |
| WO | WO-2007/010977 A1 | 1/2007 |

OTHER PUBLICATIONS

Zhou et al., Safety assessment of potential probiotic lactic acid bacterial strains Lactobacillus rhamnosus HN001, Lb. acidophilus HN017, and Bifidobacterium lactis HN019 in BALB/c mice. International Journal of Food Microbiology. vol. 56 (2000) pp. 87-96.*
Takahashi et al., Role of indigenous Lactobacilli in gastrin-mediated acid production in the mouse stomach. Applied and Environmental Microbiology, vol. 77, No. 19 (online Jul. 29, 2011) pp. 6964-6971.*
Takeshi (Japanese Patent Publication 2008-271931) machine translation, 18 pages.*
McColl and El-Omar, "Effect of H. pylori infection on gastrin and gastric acid secretion." In: Hunt, Richard & Tygat, Guido., Helicobacter pylori (Netherlands, Springer, 1994), pp. 245-256.*
Cruchet et al., Effect of the ingestion of a dietary product containing Lactobacillus johnsonii La1 on Helicobacter pylori colonization in children. Nutrition, vol. 19 (2003) pp. 716-721.*
2 to 20 years: Boys Stature-for-age and weight-for age-percentiles. Datasheet [online]. Center for Disease Control, May 30, 2000 [retrieved on Aug. 2, 2014]. Retrieved from the internet: <URL:http://www.cdc.gov/growthcharts/clinical_charts.htm#Set1>.*
2 to 20 years: Girls stature-for-age and weight-for age-percentiles. Datasheet [online]. Center for Disease Control, May 30, 2000 [retrieved on Aug. 2, 2014]. Retrieved from the internet: <URL:http://www.cdc.gov/growthcharts/clinical_charts.htm#Set1>.*
Lesbros-Pantoflickova et al., Helicobacter pylori and probiotics. The Journal of Nutrition, vol. 137 (2007) pp. 812S-818S.*
Schubert et al., Control of Gastric Acid Secretion in Health and Disease, Reviews in Basic and Clinical Gastroenterology, 2008, pp. 1842-1860, vol. 134, AGA Institute.
Uribe et al., Microflora Modulates Endocrine Cells in the Gastrointestinal Mucosa of the Rat, Gastroenterology, 1994, pp. 1259-1269, vol. 107, American Gastroenterological Association.
Kabir et al., Prevention of *Helicobacter pylori* infection by lactobacilli in a gnotobiotic murine model, Gut, 1997, pp. 49-55, vol. 41.
Labenz et al., Curing *Helicobacter pylori* Infection in Patients With Duodenal Ulcer May Provoke Reflux Esophagitis, Gastroenterology, 1997, pp. 1442-1447, vol. 112, American Gastroenterological Association.
Lind et al., The MACH2 Study: Role of Omeprazole in Eradication of *Helicobacter pylori* With 1-Week Triple Therapies, Gastroenterology, 1999, pp. 248-253, vol. 116, American Gastroenterological Association.
Office Action mailed May 24, 2011 for the corresponding Japanese Application No. 2011-013451.
Office Action mailed Feb. 27, 2013 for the corresponding Chinese Application No. 201110425172.X.
Koga, "Controlling Hyperchylia due to Lactobacillus; Examination using Axenic Animal", *Journal of Gastroenterology*, Mar. 15, 2010, vol. 107, pp. A259-216.
Myllyluoma et al., "Probiotic intervention decreases serum gastrin-17 in Helicobacter pylori infection", *Digestive and Liver Disease*, Jun. 2007,vol. 39, Issue 6, pp. 516-523.

* cited by examiner

*Primary Examiner* — Louise W Humphrey
*Assistant Examiner* — Kara Johnson
(74) *Attorney, Agent, or Firm* — Leason Ellis LLP.

(57) ABSTRACT

A method of reducing the acid concentration within gastric fluid, suppressing a tendency towards a strongly acidic pH within the gastric fluid, and inhibiting the production of gastrin involves the step of administering live or killed lactic acid bacterium (such as *Lactobacillus johnsonii* No. 1088) to a living subject. The invention also relates to a method of alleviating the side effects caused by continuous administration of a proton pump inhibitor by administering live or killed lactic acid bacterium to a living subject.

13 Claims, 5 Drawing Sheets
(1 of 5 Drawing Sheet(s) Filed in Color)

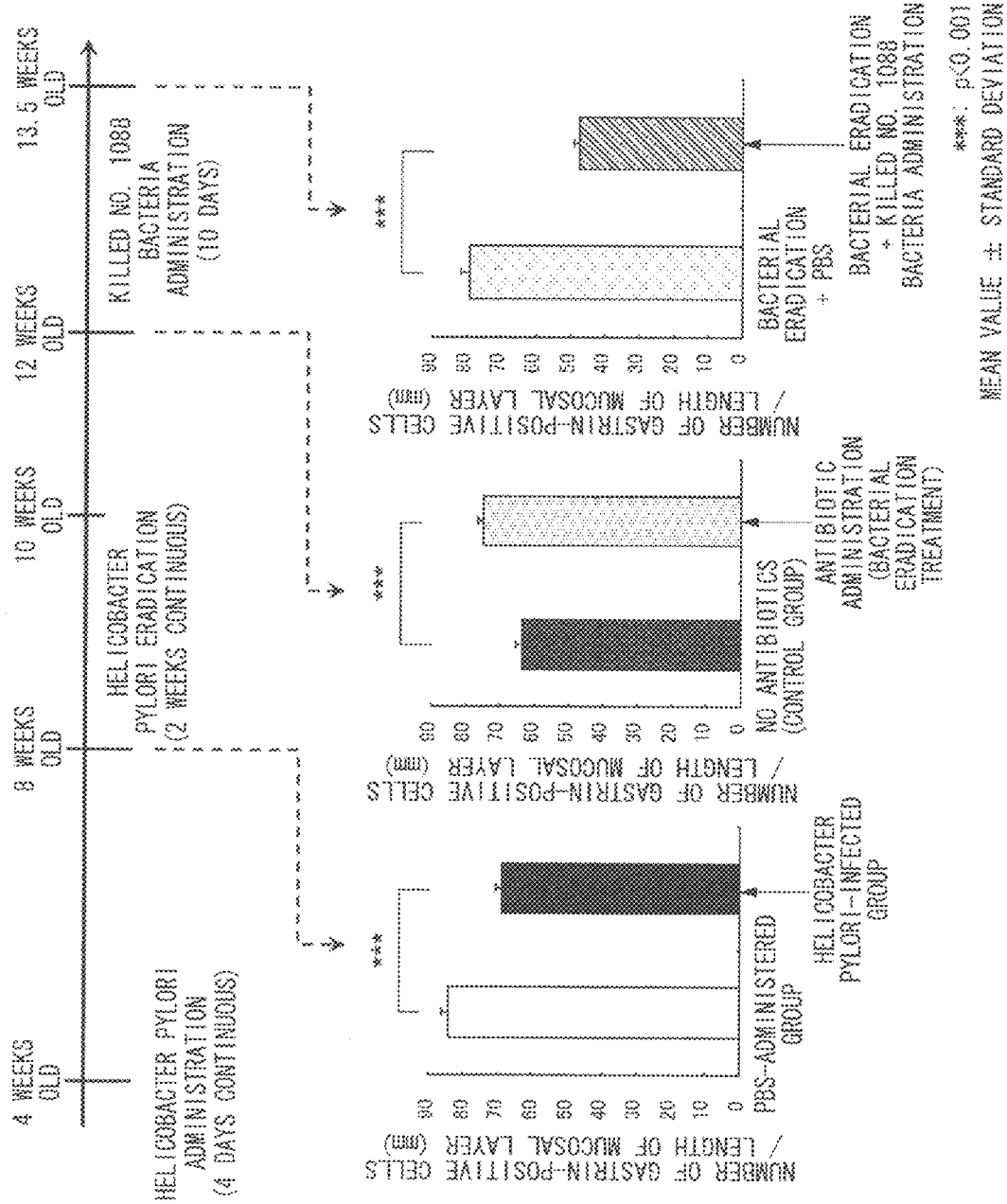

*: p<0.05
**: p<0.01
MEAN VALUE ± STANDARD DEVIATION

LACTIC ACID BACTERIUM FOR INHIBITING PRODUCTION OF GASTRIC ACID AND GASTRIN

CROSS-REFERENCE TO RELATED PATENT APPLICATIONS

Priority is claimed on Japanese Patent Application No. 2011-013451, filed Jan. 7, 2011, the content of which is incorporated herein by reference.

FIELD OF THE INVENTION

The present invention relates to a method of reducing the acid concentration within gastric fluid, suppressing a tendency towards a strongly acidic pH within the gastric fluid, and inhibiting the production of gastrin, by administering live or killed lactic acid bacterium to a living subject. Further, the invention also relates to a method of alleviating the side effects caused by continuous administration of a proton pump inhibitor (hereinafter abbreviated as PPI) by administering live or killed lactic acid bacterium to a living subject.

BACKGROUND OF THE INVENTION

Gastrin, which is produced within the pyloric region of the stomach, is a hormone that has the effect of increasing the acid concentration within the gastric fluid and shifting the pH of the gastric fluid to a strongly acidic state (Schubert M L, Peura D A. *Gastroenterology*, 134: 1842 to 1860, 2008). In other words, by inhibiting the production of gastrin, the acid concentration within the gastric fluid can be reduced, and the tendency towards a highly acidic pH can be suppressed.

It has been reported that, in the stomachs of rats, there are indications that the production of gastrin is inhibited by the existence of bacteria (Uribe A, et al. *Gastroenterology*, 107: 1259 to 1269, 1994). Further, the stomachs of humans exist in a substantially-germ-free state, and compared with the stomachs of rodents, the acid concentration of the gastric fluid is higher, and the pH is more strongly acidic (Kabir A M, et al. *Gut*, 41: 49 to 55, 1997). One example of a bacterium that can reside in the human stomach is *Helicobacter pylori*, which is a known pathogenic bacterium. It has been reported that when the *Helicobacter pylori* is eradicated from an infected patient, the acid concentration within the gastric fluid increases, and the incidence rate of reflux esophagitis increases (Labenz J, et al. *Gastroenterology*, 112: 1442 to 1447, 1997).

*Lactobacillus johnsonii* No. 1088 (hereinafter abbreviated as "No. 1088") is a lactic acid bacterium of the genus *Lactobacillus* that has been developed by the inventors of the present invention, and because this bacterium was isolated from the gastric fluid of humans, it has extremely good acid resistance and is able to exist within the human stomach. Further, the bacterium has a powerful growth-inhibitory effect on pathogenic bacteria (such as *Escherichia coli* O-157 and *Helicobacter pylori*), and is an extremely useful bacterial strain even among the various bacteria of the genus *Lactobacillus* (accession number: NITE BP-278).

Problems to be Solved by the Invention

If the acid concentration within the gastric fluid is high, namely if a state of hyperchlorhydria exists, then when gastric fluid is refluxed up into the esophagus, the epithelial cells of the esophagus are damaged, causing inflammation. In mild cases, this process yields symptoms of heartburn, whereas in severe cases, it can cause reflux esophagitis. Moreover, if this situation is allowed to persist, then it may cause degeneration or cancerations of the esophageal tissue, resulting in the development of Barrett's esophageal cancer or the like. Further, in recent years, for reasons including a gradual westernization of the diet in Japan, the actions of the sphincter muscles that exist at the extremities of the esophagus have tended to weaken, thus increasing the likelihood of gastric acid reflux. The incidence rates of reflux esophagitis and Barrett's esophageal cancer in Japan are currently on the increase.

It has been reported that when the *Helicobacter pylori* is eradicated from an infected patient, the acid concentration within the gastric fluid increases and the risk of developing reflux esophagitis also increases (Labenz J, et al. *Gastroenterology*, 112: 1442 to 1447, 1997).

Medical treatment for peptic ulcers such as gastric ulcers and duodenal ulcers often uses continuous administration of a PPI that inhibits the secretion of gastric acid, but one known side effect of this treatment is excessive production of gastrin. Animal tests have proven that this excess gastrin can cause excessive proliferation and enlargement of the gastric mucosal cells, and bloating of the stomach tissue. Clinical trials in humans have resulted in similar indications. Moreover, it is known that when use of the PPI is halted due to remission of the peptic ulcer or the like, the state of excess gastrin can cause symptoms such as excessive gastric acid secretion and the like (Schubert M L, Peura D A. *Gastroenterology*, 134: 1842 to 1860, 2008).

In order to address the issues described above, the development of a method of inhibiting the production of gastric acid and gastrin is essential.

SUMMARY OF THE INVENTION

Means to Solve the Problems

The present invention address the issues described above, and provides a method of inhibiting gastrin production by using a bacterium that acts within the stomach without causing pathogenicity. This method inhibits the production of gastrin by administering live or killed lactic acid bacterium to a living subject.

Another aspect of the present invention that address the issues described above provides a method of alleviating side effects caused by continuous administration of a PPI by administering live or killed lactic acid bacterium.

The present invention relates to a method of inhibiting production of gastric acid or gastrin by administering live or killed lactic acid bacterium, and various products such as pharmaceutical products and health foods that use the method.

The present invention also relates to a method of alleviating side effects of a gastric acid secretion inhibitor (such as a proton pump inhibitor) by administering live or killed lactic acid bacterium, and various products such as pharmaceutical products and health foods that use the method.

The lactic acid bacterium is a *Lactobacillus johnsonii* No. 1088 (accession number: NITE BP-278).

That is, the present invention relates to following (1) to (9).
(1) A method of inhibiting production of gastric acid or gastrin including administering an effective dose of live or killed lactic acid bacterium to a subject in need thereof.
(2) A method of alleviating side effects of a gastric acid secretion inhibitor comprising administering an effective dose of live or killed lactic acid bacterium to a subject in need thereof.

(3) The method of inhibiting production of gastric acid or gastrin according to (1), wherein the lactic acid bacterium is a *Lactobacillus johnsonii* No. 1088 (accession number: NITE BP-278).

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 4 Promotion of gastrin production by eradication of *Helicobacter pylori*, and suppression of the promotion by administration of killed No. 1088.

DETAILED DESCRIPTION OF THE INVENTION

Embodiments of the Invention

Figure 1:
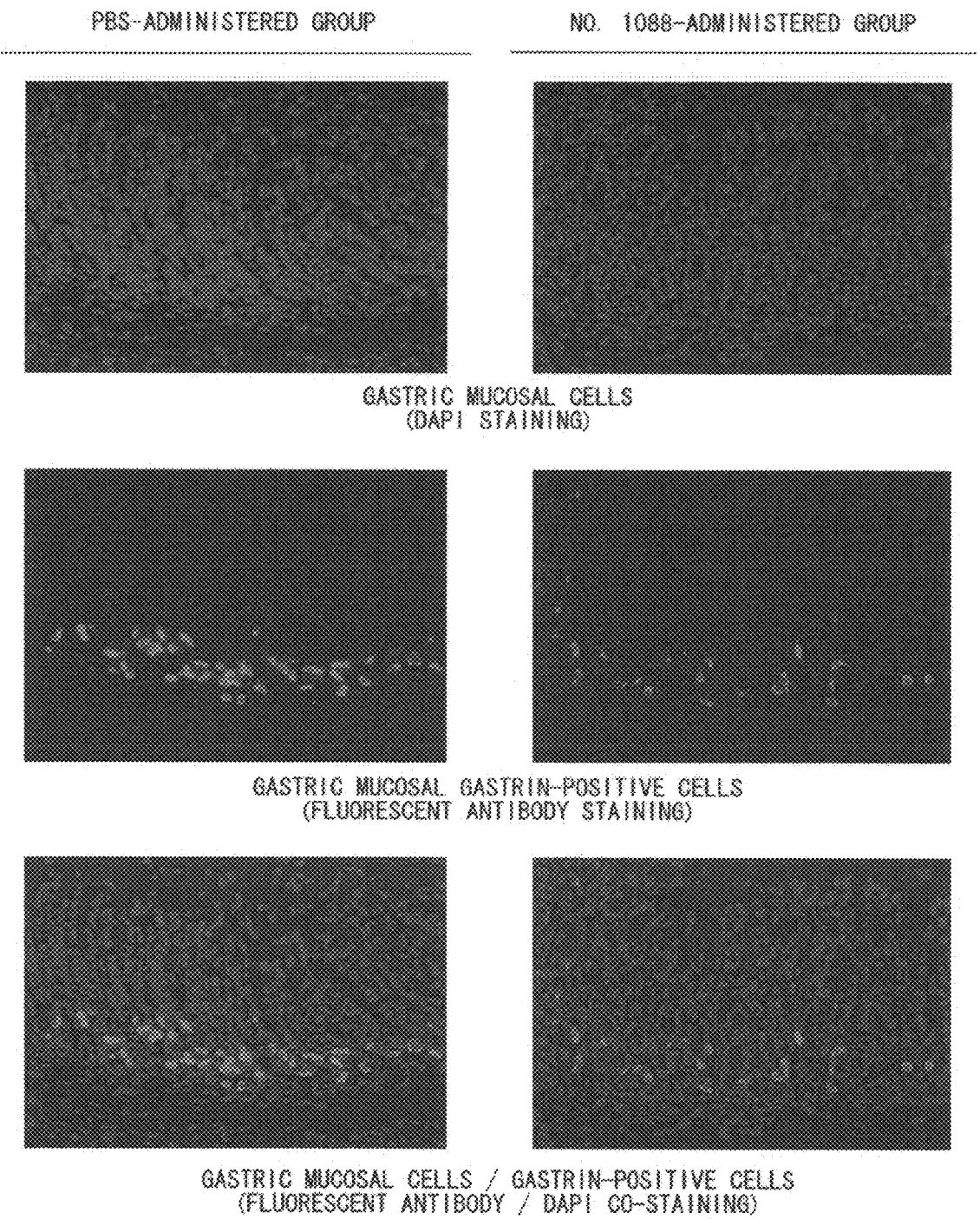
FIG. 1 Fluorescence microscope images of gastrin-positive cells within stomach tissue using immunostaining, and reduction in number of gastrin-positive cells by administration of live No. 1088.

There are no particular limitations on the living organism that represents the subject requiring inhibition of the production of gastric acid or gastrin within the present invention, provided the subject is an animal that secretes gastric acid or gastrin, although the subject is preferably a mammal, and more preferably a human.

Similarly, there are no particular limitations on the living organism that represents the subject requiring alleviation of side effects of a gastric acid secretion inhibitor within the present invention, provided the subject is an animal that secretes gastric acid or gastrin, although the subject is preferably a mammal, and more preferably a human.

<Lactic Acid Bacterial Strain>

The *Lactobacillus johnsonii* No. 1088 that represents the lactic acid bacterial strain of the present invention was deposited with the National Institute of Technology and Evaluation Patent Microorganisms Depository (2-5-8 Kazusakamatari, Kisarazu-shi, Chiba, Japan (zip code: 292-0818)) on Nov. 14, 2006 with the accession number NITE P-278, and was transferred to the International Depositary Authority as NITE BP-278.

The above strain No. 1088 has a powerful growth-inhibitory effect on pathogenic bacteria (such as *Escherichia coli* O-157 and *Helicobacter pylori*), and also has the effect of inhibiting gastrin production. Further, the strain No. 1088 can also reduce the acid concentration within gastric fluid, and inhibit the tendency for the pH of gastric fluid to become strongly acidic and the tendency for the production of gastrin to be promoted by administration of a PPI. Moreover, the strain No. 1088 can also alleviate the side effects of gastric acid secretion inhibitors such as PPIs.

The bacteriological properties of the strain No. 1088 and a method of preparing No. 1088 are disclosed in Japanese Patent (Granted) Publication No. 4,457,364.

<Method of Administration>

There are no particular limitations on the method used for administering the live or killed lactic acid bacterium of the present invention, and an appropriate method may be selected in accordance with the intended purpose. One example of the administration method is oral administration.

The live or killed lactic acid bacterium of the present invention may be administered alone. Alternatively, the live or killed lactic acid bacterium may be formulated into any of various dosage forms together with one or more pharmaceutically acceptable additives in accordance with the selected mode of administration, and subsequently administered to the subject.

Further, in addition to the live or killed lactic acid bacterium described above, the gastric acid or gastrin production inhibitor of the present invention and the gastric acid secretion inhibitor side effect alleviation agent of the present invention may also include pharmaceutically acceptable additives, provided the addition of these additives does not impair the effects of the present invention.

Examples of additives that may be used include various additives typically used in the field of pharmaceutical formulations, and specific examples include *L. johnsonii* No. 1088, *L. acidophilus* JCM 1132, and *L. gasseri* LG21.

Examples of dosage forms that may be formulated using these additives include solid formulations such as tablets, capsules, granules and powders, and liquid formulations such as syrups and elixirs, and these formulations may be prepared in accordance with typical methods used in the field of pharmaceutical formulations. Liquid formulations that are prepared at the time of use by dissolution or dispersion within water or another appropriate solvent may also be used. Furthermore, dissolution or dispersion within a physiological saline solution or glucose solution may also be used if required, and a buffer or preservative may also be added if necessary.

These formulations may also include other compounds that are effective for the medical treatment. Examples of these other compounds include yeasts such as beer yeast, dietary fiber such as guar fiber, vitamins such as vitamin $B_1$, vitamin $B_2$, vitamin $B_6$ and vitamin C sodium, sugars such as lactosucrose, β-cyclodextrin (β-CD) and lactose, sugar alcohols such as erythritol, fruit juices such as lemon juice micron and lemon micron, anticaking agents such as Sylopage (manufactured by Fuji Silysia Chemical Ltd.), and hardened oils such as Lubriwax (a registered trademark) (manufactured by Freund Corporation).

<Effective Amount>

An effective amount of the present invention refers to the amount of the active compound or pharmaceutical substance that evokes a biological or pharmaceutical response within the tissue, system, animal or human subject, and is an amount that is determined by researchers, veterinarians, doctors or other clinicians. Specifically, an effective amount of the present invention refers to the amount of the live or killed lactic acid bacterium of the present invention which, upon administration to the subject, yields a gastric acid or gastrin production-inhibiting effect, or an effect that alleviates the side effects of a gastric acid secretion inhibitor.

The effective amount of the present invention varies depending on factors such as the administration target organism and the administration dosage form, and may be selected appropriately in accordance with, for example, the administration target organism or the degree of side effects observed within the administration target organism. In those cases where the gastrin production inhibitor or the gastric acid secretion inhibitor side effect alleviation agent of the present invention is used as a pharmaceutical agent, an appropriate effective amount may be selected by researchers, veterinarians, doctors or other clinicians.

In those cases where live or killed lactic acid bacterium of the present invention are used as a gastric acid or gastrin production inhibitor, or as a gastric acid secretion inhibitor side effect alleviation agent or the like, the effective amount of the bacteria and the number of administered doses may be altered in accordance with the administration target organism, the gender, age, bodyweight and symptoms of the target organism, and the type and degree of effect being targeted.

Further, the effective amount in humans is typically within a range from $2\times10^8$ CFU to $1\times10^9$ CFU per kg of bodyweight per day, and this amount may be administered in a single dose, or divided into two or more doses.

<Gastric Acid or Gastrin Production Inhibitor, and Gastric Acid Secretion Inhibitor Side Effect Alleviation Agent>

A gastric acid or gastrin production inhibitor, and a gastric acid secretion inhibitor side effect alleviation agent according to the present invention include an effective amount of live or killed lactic acid bacterium of the present invention. This lactic acid bacterium is preferably *Lactobacillus johnsonii* No. 1088.

By including an effective amount of live or killed bacteria of No. 1088, the gastric acid or gastrin production inhibitor and the gastric acid secretion inhibitor side effect alleviation agent are able to respectively inhibit the production of gastric acid or gastrin, and alleviate the side effects caused by continuous administration of a proton pump inhibitor (PPI).

The gastric acid secretion inhibitor side effect alleviation agent of the present invention is effective for a variety of gastric acid secretion inhibitors, and is particularly effective in reducing the side effects of PPIs.

<Food Items>

The live or killed lactic acid bacterium according to the present invention may also be added to food items.

Specific examples of such food items according to the present invention include yoghurts and cheeses.

EXAMPLES

The present invention is based partially on the test results described below.

1. Inhibition of Gastric Acid and Gastrin Production by Administering Live No. 1088

1-1) Preparation of Live No. 1088 Administered Mice

Two groups of mice were prepared, each containing seven 8-week old germ-free (GF) Balb/c male mice (reared within an isolator, Tokai University School of Medicine). One group was administered orally with a suspension prepared by suspending $1\times10^9$ CFU of live No. 1088 in a phosphate buffer solution (PBS), and the other group was administered orally with an equal volume of PBS.

1-2) Preparation of Stomach Tissue Sections 10 days after administration, each of the mice was killed, and the stomach was extracted, immersed in 10% formalin (Wako Pure Chemical Industries, Ltd.)—PBS, and fixed overnight at room temperature. Subsequently, the fixed stomach tissue was immersed in ethanol, immersed in xylene, and then embedded in paraffin. The paraffin-embedded sample was sliced thinly into sections having a thickness of 2 μm using a microtome, and these sections were then stuck to silane-coated slide glasses (Muco Pure Chemicals Co, Ltd.) and dried overnight at 62° C.

1-3) Gastrin Immunostaining Using Stomach Tissue Sections

The prepared sections were treated with xylene and ethanol to effect deparaffinization, and were than microwaved for 10 minutes at 98° C. using a Target retrieval solution (Dako A/S) to activate the antigens. The tissue sections were then reacted overnight at 4° C. with Rabbit polyclonal anti-gastrin antibody (Dako A/S) as a primary antibody, subsequently reacted for two hours at room temperature with Goat anti-rabbit IgG Alexa 488 antibody (Molecular Probe) as a secondary antibody, and then mounted using an antifade mounting medium containing added DAPI that stains the cell nuclei.

1-4) Observation Using Fluorescence Microscope

The fluorescent dye DAPI bonded to the cell DNA, and the tissue sections stained with the anti-gastrin antibody were subjected to observation and image capture using a fluorescence microscope BZ-9000 (Keyence Corporation). The results are shown in FIG. 1. As shown in the figure, administration of live No. 1088 caused no significant change in the number of cells within the gastric mucosal tissue as identified by DAPI staining, but a reduction was confirmed for the number of gastrin-positive cells identified by anti-gastrin antibody staining. In other words, the results indicated that administration of live No. 1088 inhibits the production of gastrin.

1-5) Statistical Analysis of Number of Gastrin-Positive Cells

Figure 2:
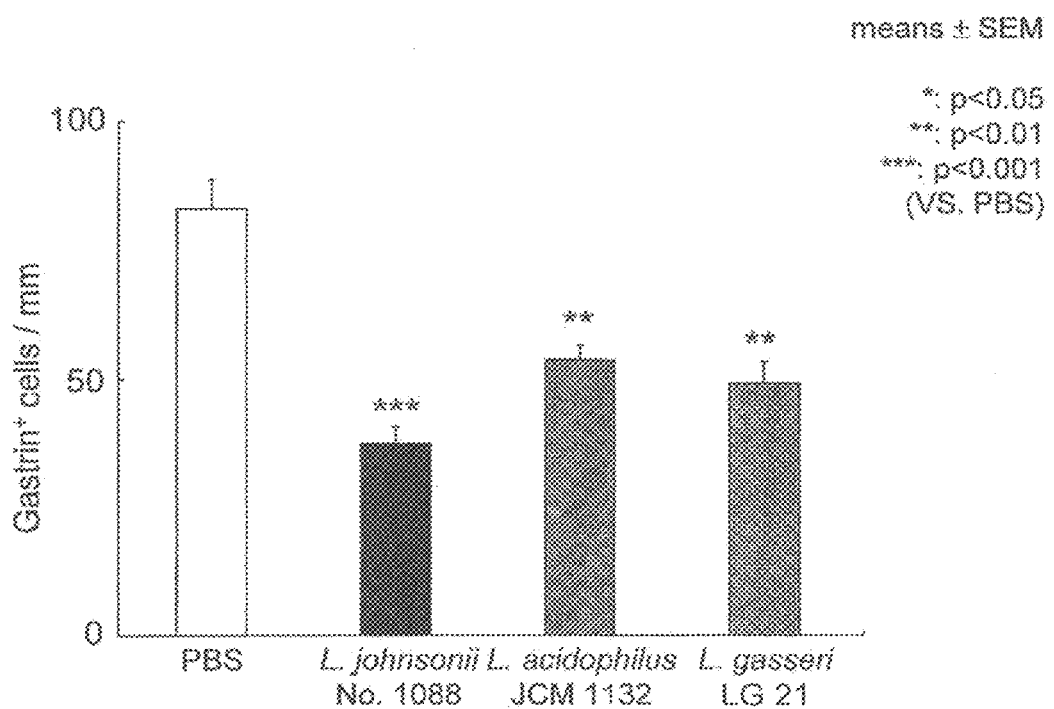
FIG. 2 Inhibition of gastrin production by administration of live No. 1088, *L. acidophilus* JCM 1132 and *L. gasseri* LG21.

In order to enable statistical analysis of the change in gastrin production for each group based on the tissue sections, the length of the mucosal layer of the pyloric region of the stomach within each tissue photograph was measured using AxioVision software (Carl Zeiss MicroImaging GmbH), the number of gastrin-positive cells therein was counted by visual inspection, and the number of gastrin-positive cells per unit length (1 mm) was calculated. The results of analyzing the obtained numerical values by a Mann-Whitney U test using SPSS software (IBM SPSS) are shown in FIG. 2. The live No. 1088 administered group exhibited a statistically significant reduction of at least 50% compared with the PBS-administered group. In other words, the results indicated that administering live No. 1088 inhibited the production of gastrin. Further, a similar phenomenon was confirmed for administration of live bacteria of *Lactobacillus acidophilus* JCM.1132 and *Lactobacillus gasseri* LG21.

2. Reduction of the Acid Concentration within Gastric Fluid and Suppression of Tendency Towards a Strongly Acidic pH by Administering Live No. 1088

2-1) Preparation of Live No. 1088-Administered Mice

Two groups of mice were prepared, each containing five 8-week old GF-Balb/c male mice. One group was administered orally with a suspension prepared by suspending $1\times10^9$ CFU of live No. 1088 in PBS, and the other group was administered orally with an equal volume of PBS.

2-2) Measurement of Acid Concentration and pH of Gastric Fluid 10 days after administration, the mice and PBS-administered mice were each anesthetized using Nembutal, and subsequently secured to an operating table. A laparotomy was performed, the esophagus adjacent to the cardiac region of the stomach and the duodenum adjacent to the pyloric region of the stomach were clipped with forceps, and following standing for two hours, the gastric fluid accumulated inside the stomach was extracted. The acid concentration within the extracted gastric fluid was measured by performing an acid-base titration using a 0.1 N aqueous solution of sodium hydroxide (Wako Pure Chemical Industries, Ltd.). Further, the pH was measured using a pH meter (Horiba, Ltd.). The results of analyzing the numerical values obtained for each of the samples by performing a Mann-Whitney U test using SPSS are shown in Table 1. The No. 1088-administered group exhibited a statistically significant reduction in the acid concentration within the gastric fluid and a statistically significant weaker acidic pH level. In other words, the results indicated that the gastrin production-inhibiting effect exhibited by the No. 1088 reduces the acid concentration within the gastric fluid and suppresses the tendency towards a strongly acidic pH.

TABLE 1

Reduction of the acid concentration within Gastric Fluid and Suppression of Tendency Towards a Strongly Acidic pH by Administering Live No. 1088

|  | Gastric fluid volume (mL) | Acid concentration (µEq/mL) | pH |
|---|---|---|---|
| PBS-administered mice | 0.6 ± 0.2 | 19.0 ± 4.4 | 3.0 ± 0.5 |
| No. 1088-administered mice | 0.6 ± 0.3 | 5.2 ± 5.1* | 6.1 ± 0.7** |

*p < 0.05
**p < 0.01

3. Inhibition of Gastrin Production by Administering Killed Bacteria of No. 1088

3-1) Preparation of Killed No. 1088 Administered Mice

Two groups of mice were prepared, each containing five 8-week old GF-Balb/c male mice. One group was administered orally with a suspension prepared by suspending an amount of killed No. 1088 equivalent to $1 \times 10^9$ CFU of live bacteria in PBS, and the other group was administered orally with an equal volume of PBS. Administration was performed once per day for 10 days.

3-2) Preparation of Stomach Tissue Sections 24 hours after the final administration, each of the mice was killed, and the stomach was extracted, immersed in 10% formalin-PBS, and fixed overnight at room temperature. Subsequently, the fixed stomach tissue was immersed in ethanol, immersed in xylene, and then embedded in paraffin. The paraffin-embedded sample was sliced thinly into sections having a thickness of 2 µm using a microtome, and these sections were then stuck to silane-coated slide glasses and dried overnight at 62° C.

3-3) Gastrin Immunostaining Using Stomach Tissue Sections

The prepared sections were treated with xylene and ethanol to effect deparaffinization, and were than microwaved for 10 minutes at 98° C. using a Target retrieval solution to activate the antigens. The tissue sections were then reacted overnight at 4° C. with Rabbit polyclonal anti-gastrin antibody as a primary antibody, subsequently reacted for two hours at room temperature with Goat anti-rabbit IgG Alexa 488 antibody as a secondary antibody, and then mounted using an antifade mounting medium.

3-4) Observation Using Fluorescence Microscope

The stained tissue sections were subjected to observation and image capture using a fluorescence microscope BZ-9000. Comparison of the killed No. 1088 administered group and the PBS-administered group indicated that the number of gastrin-positive cells had been reduced in the killed No. 1088 administered group.

3-5) Statistical Analysis of Number of Gastrin-Positive Cells

Figure 3:
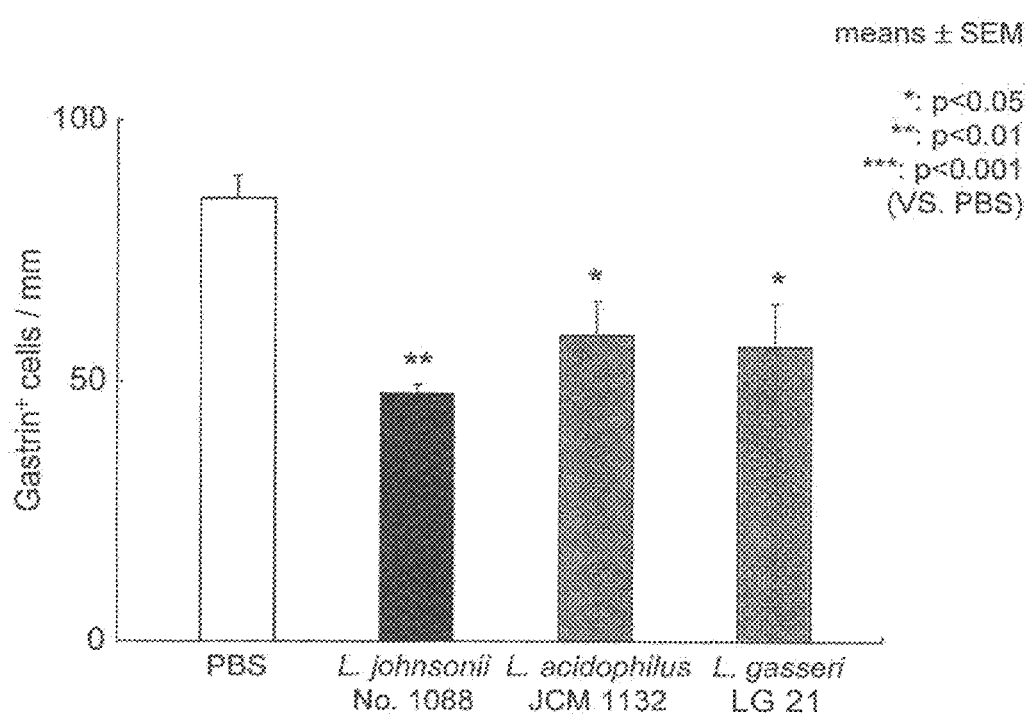
FIG. 3 Inhibition of gastrin production by administration of killed No. 1088, *L. acidophilus* JCM 1132 and *L. gasseri* LG21.

In order to enable statistical analysis of the change in gastrin production for each group based on the tissue sections, the length of the mucosal layer of the pyloric region of the stomach within each tissue photograph was measured using AxioVision software, the number of gastrin-positive cells therein was counted by visual inspection, and the number of gastrin-positive cells per unit length (1 mm) was calculated. The results of analyzing the obtained numerical values by a Mann-Whitney U test using SPSS are shown in FIG. 3. The No. 1088 killed bacteria-administered group exhibited a statistically significant reduction of at least 40% compared with the PBS-administered group. In other words, the results indicated that not only the administration of live No. 1088 but also the administration of killed No. 1088 inhibited the production of gastrin. Further, a similar phenomenon was confirmed for administration of killed bacteria of *Lactobacillus acidophilus* JCM1132 and *Lactobacillus gasseri* LG21.

4. Promotion of Gastrin Production by Eradication of *Helicobacter pylori*, and Inhibition of this Promotion by Administering Killed No. 1088

4-1) Preparation of *Helicobacter pylori*-Carrying Mice

Six groups of mice were prepared, each containing five 4-week old GF-Balb/c male mice. Five of these groups were administered orally for 4 days with a suspension prepared by suspending $1 \times 10^9$ CFU of live *Helicobacter pylori* in PBS, and the remaining group was administered orally for 4 days with an equal volume of PBS. Four weeks after administration of the *Helicobacter pylori*, one group of the *Helicobacter pylori*-carrying mice and the PBS-administered group were killed and embedded in paraffin using the procedure described above. Three of the remaining groups of *Helicobacter pylori*-carrying mice were subjected to the same treatment as that used to eradicate *Helicobacter pylori* in humans (Lind T, et al. *Gastroenterology*, 116: 248 to 253, 1999), and the reaming one group was kept as a non-eradicated control group by administering a solution containing no added antibiotics. These administrations were performed continuously for two weeks. Two weeks after completion of the bacterial eradication treatment, one of the bacterial eradication treatment groups and the non-eradicated control group were killed and embedded in paraffin using the procedure described above. Of the remaining bacterial eradication treatment groups, one group was administered orally with a suspension prepared by suspending an amount of killed bacteria of No. 1088 equivalent to $1 \times 10^9$ CFU of live bacteria in PBS, using the same procedure as that described above, and the other group was administered orally with an equal volume of PBS. Administration was performed once per day for 10 days, and 24 hours after the final administration, the mice were killed and embedded in paraffin using the procedure described above. The preparation processes for each of the groups of mice described above are shown in stages in FIG. 4.

4-2) Preparation of Stomach Tissue Sections

The paraffin-embedded blocks obtained using the procedure described above were sliced thinly into sections having a thickness of 2 µm using a microtome, and these sections were then stuck to silane-coated slide glasses and dried overnight at 62° C.

4-3) Gastrin Immunostaining Using Stomach Tissue Sections

The prepared sections were treated with xylene and ethanol to effect deparaffinization, and were than microwaved for 10 minutes at 98° C. using a Target retrieval solution to activate the antigens. The tissue sections were then reacted overnight at 4° C. with Rabbit polyclonal anti-gastrin antibody as a primary antibody, subsequently reacted for two hours at room temperature with Goat anti-rabbit IgG Alexa 488 antibody as a secondary antibody, and then mounted using an antifade mounting medium.

4-4) Observation Using Fluorescence Microscope

The stained tissue sections were subjected to observation and image capture using a fluorescence microscope BZ-9000. The results revealed, firstly, that when the *Helicobacter pylori*-carrying mice were compared with the *Helicobacter pylori* non-infected mice (the PBS-administered group), the number of gastrin-positive cells had been reduced in the *Helicobacter pylori*-carrying mice. Secondly, it was confirmed that the mice in which the *Helicobacter pylori* had been eradicated had an increased number of gastrin-positive cells compared with the non-eradicated mice. Moreover, comparison of the group that was administered with the killed No. 1088 following eradication of the *Helicobacter pylori* and the group that was administered with PBS following eradication of the *Helicobacter pylori* revealed that the killed No. 1088 administered group exhibited a reduced number of gastrin-positive cells.

4-5) Statistical Analysis of Number of Gastrin-Positive Cells

In order to enable statistical analysis of the change in gastrin production for each group within the above samples based on the tissue sections, the length of the mucosal layer of the pyloric region of the stomach within each tissue photograph was measured using AxioVision software, the number of gastrin-positive cells therein was counted by visual inspection, and the number of gastrin-positive cells per unit length (1 mm) was calculated. The results of analyzing the obtained numerical values for each of the samples at the various ages of sample extraction by a Mann-Whitney U test using SPSS are shown in FIG. 4. Firstly, comparison of the *Helicobacter pylori*-carrying mice and the *Helicobacter pylori* non-infected mice (the PBS-administered group) confirmed a significant reduction in the number of gastrin-positive cells in the *Helicobacter pylori*-carrying mice. Secondly, in the mice in which the *Helicobacter pylori* had been eradicated, a significant increase in the number of gastrin-positive cells was confirmed compared with the non-eradicated mice. Moreover, comparison of the group that was administered with the killed No. 1088 following eradication of the *Helicobacter pylori* and the group that was administered with PBS following eradication of the *Helicobacter pylori* confirmed a significant reduction of approximately 40% in the number of gastrin-positive cells in killed No. 1088 administered group. In other words, the results indicated that the excess gastric acid and enhanced risk of reflux esophagitis observed in humans upon eradication of *Helicobacter pylori* is caused by increased gastrin production, and that administration of killed No. 1088 is able to inhibit this promotion of gastrin production.

An example of the method of alleviating the side effects caused by continuous administration of a PPI according to the present invention is described below, but the present invention is not limited to the No. 1088 used in the following example, and applies to live or killed bacteria of all lactic acid bacteria.

5. Side Effects Caused by Continuous PPI Administration, and Alleviation of Those Side Effects by Administering No. 1088

5-1) Preparation of Live No. 1088 Administered Mice

Six groups of mice were prepared, each containing five 4-week old GF-Balb/c male mice. Three of the groups were administered orally with a suspension prepared by suspending $1 \times 10^9$ CFU of live No. 1088 in PBS, and the remaining three groups were administered orally with an equal volume of PBS.

5-2) Continuous Administration of PPI

When the mice reached 8 weeks of age, a treatment was started for one group of the No. 1088-administered mice and one group of the PBS-administered mice in which the mice were administered subcutaneously every other day with a solution prepared by dissolving 200 μg of the PPI Omeprazole (AstraZeneca Ltd.) in 200 μL of PBS (8 weeks of continuous PPI administration). When the mice reached 12 weeks of age, a similar treatment was started for one more of each of the groups (4 weeks of continuous PPI administration), and the remaining two groups were used as control groups that were not administered with Omeprazole.

5-3) Measurement of Stomach Weight and Preparation of Stomach Tissue Sections

Upon reaching 16 weeks of age, the mice of each group were killed, and following measurement of the bodyweight, the stomach was extracted from each mouse, the stomach contents (feed and the like) were removed by washing with PBS, and the stomach weight was measured. Subsequently, the extracted stomach tissue was immersed in 10% formalin-PBS and fixed overnight at room temperature. The fixed stomach tissue was then immersed in ethanol, immersed in xylene, and then embedded in paraffin. The paraffin-embedded sample was sliced thinly into sections having a thickness of 2 μm using a microtome, and these sections were then stuck to silane-coated slide glasses and dried overnight at 62° C.

5-4) Gastrin Immunostaining Using Stomach Tissue Sections

The prepared sections were treated with xylene and ethanol to effect deparaffinization, and were than microwaved for 10 minutes at 98° C. using a Target retrieval solution to activate the antigens. The tissue sections were then reacted overnight at 4° C. with Rabbit polyclonal anti-gastrin antibody as a primary antibody, subsequently reacted for two hours at room temperature with Goat anti-rabbit IgG Alexa 488 antibody as a secondary antibody, and then mounted using an antifade mounting medium.

5-5) Observation Using Fluorescence Microscope

The stained tissue sections were subjected to observation and image capture using a fluorescence microscope BZ-9000. The results confirmed that for the PBS-administered mice, PPI administration increased the number of gastrin-producing cells. In contrast, for the live No. 1088 administered mice, the PPI administration caused no increase or decrease in the number of gastrin-producing cells. In other words, the results indicated that administration of live No. 1088 inhibits the promotion of gastrin production caused by the PPI.

Figure 5A:
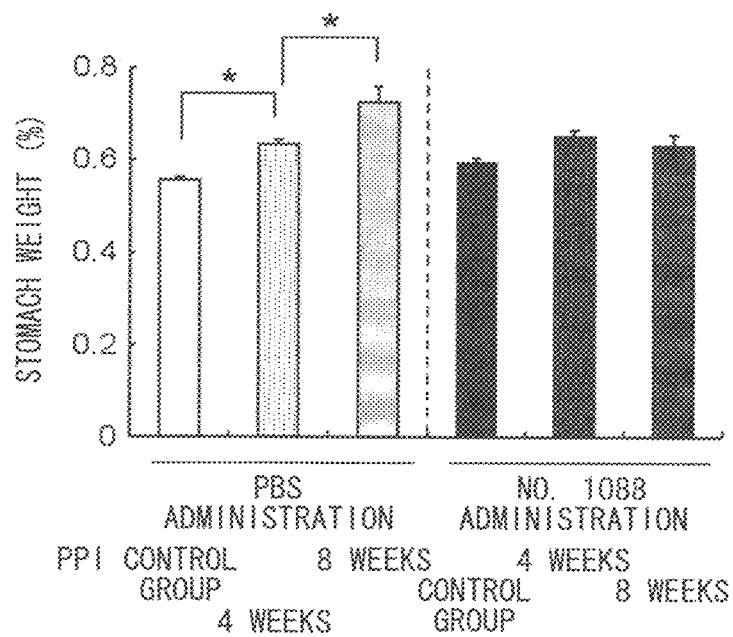
FIG. 5A Statistical analyses of stomach weight ratio.
Figure 5B:
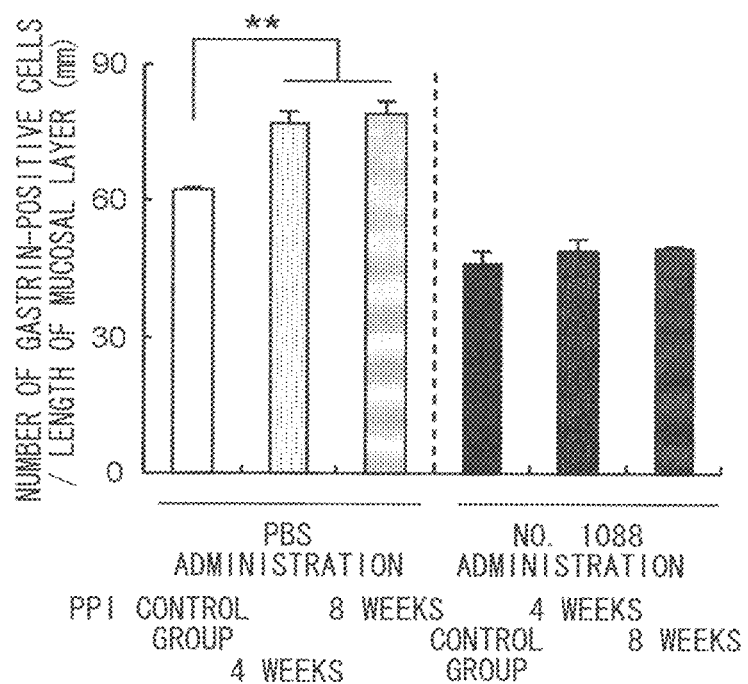
FIG. 5B Statistical analyses of number of gastrin-positive cells.

5-6) Statistical Analyses of Stomach Weight and Number of Gastrin-Positive Cells Using the bodyweights and stomach weights measured upon extraction of the stomachs from the samples of each group, the ratio (%) of stomach weight to bodyweight was calculated for each group. Further, in order to enable statistical analysis of the change in gastrin production for each group based on the tissue sections, the length of the mucosal layer of the pyloric region of the stomach within each tissue photograph was measured using AxioVision software, the number of gastrin-positive cells therein was counted by visual inspection, and the number of gastrin-positive cells per unit length (1 mm) was calculated. The results of analyzing the obtained numerical values by a Kruskal-Wallis T test using SPSS are shown in FIG. 5A for the ratio of stomach weight to bodyweight, and in FIG. 5B for the number of gastrin-positive cells. In the PBS-administered mice, administration of the PPI caused significant increases in both the stomach weight ratio and the number of gastrin-producing cells, with the increases proportional to the length of the administration period. In contrast, in the No. 1088-administered mice, administration of the PPI caused no increase or decrease in the stomach weight ratio or the number of gastrin-producing cells. In other words, the results indicated that the side effects caused by continuous PPI administration, such as excessive gastrin production, excessive proliferation and enlargement of the gastric mucosal cells, and bloating of the stomach tissue, can be alleviated by administration of a lactic acid bacterium typified by No. 1088.

6. Examples of Formulations 6-1) Formulation Example 1

54.67 g of beer yeast, 54.67 g of guar fiber, 0.55 g of vitamin $B_1$, 0.55 g of vitamin $B_2$, 0.55 g of vitamin $B_6$, 109.34 g of vitamin C sodium, 82.01 g of lactosucrose, 348.26 g of CD, 32.80 g of lemon juice micron, 328.03 g of lactose and 328.03 g of erythritol were combined and mixed with an appropriate amount of added water, and the mixture was then dried. Following drying, the mixture was sieved to prepare granules of 0.3 mm to 0.5 mm. No. 1088 was freeze dried using the method disclosed in Example 1 of Japanese Patent (Granted) Publication No. 4,457,364, and 100 g of the thus obtained dried bacteria No. 1088, 30 g of lemon micron, 20 g of Sylopage, and 10 g of Lubriwax (a registered trademark) were sprayed onto the above granules and mixed uniformly to complete the preparation.

This formulation may also include other compounds that are effective for medical treatment.

INDUSTRIAL APPLICABILITY

As described above, administration of live or killed lactic acid bacterium was shown to inhibit the production of gastric acid and gastrin. In other words, ingestion of the live or killed lactic acid bacterium can be used in pharmaceutical products, functional foods or health foods or the like that enable control of acid concentration within the gastric fluid and stabilization of the gastric fluid pH. Further, administration of the live or killed lactic acid bacterium can be used in pharmaceutical products and the like that alleviate the side effects of gastric acid secretion inhibitors typified by PPIs.

What is claimed is:

1. A method of inhibiting production of gastric acid or gastrin comprising the step of:
administering a live or killed lactic acid bacterium to a subject in need thereof in a dose effective to inhibit production of gastric acid or gastrin, wherein
the dose is in a range from $2\times10^8$ CFU to $1\times10^9$ CFU per kg of bodyweight per day, and
the subject is selected from the group consisting of: one who has hyperchlorhydria; one who is in a state of excessively producing gastric acid after eradication of *Helicobacter pylori*; one who has reflux esophagitis; one who has Barrett's esophageal cancer; and one who is in a state of excessively producing gastrin by continuous administration of a gastric acid secretion inhibitor.

2. The method of claim 1 for alleviating side effects of a gastric acid secretion inhibitor.

3. The method of inhibiting production of gastric acid or gastrin according to claim 1, wherein the lactic acid bacterium is a *Lactobacillus johnsonii* No. 1088 (accession number: NITE BP-278).

4. The method of inhibiting production of gastric acid or gastrin according to claim 3, wherein the subject in need thereof is a human.

5. The method of inhibiting production of gastric acid or gastrin according to claim 3, wherein the lactic acid bacterium is administered in a single dose or divided into two or more doses per day.

6. The method of inhibiting production of gastric acid or gastrin according to claim 1, wherein the subject in need thereof is a human.

7. The method of inhibiting production of gastric acid or gastrin according to claim 1, wherein the lactic acid bacterium is administered in a single dose or divided into two or more doses per day.

8. A method of treating hyperchlorhydria or excessive production of gastrin comprising the step of:
administering live or killed lactic acid bacterium to a subject in need thereof in a dose effective to treat hyperchlorhydria or excessive production of gastrin, wherein
the dose is ins a range from $2\times10^8$ CFU to $1\times10^9$ CFU per kg of bodyweight per day, and the subject is selected from the group consisting of: one who has hyperchlorhydria; one who is in a state of excessively producing gastric acid after eradication of *Helicobacter pylori*; one who has reflux esophagitis; one who has Barrett's esophageal cancer; and one who is in a state of excessively producing gastrin by continuous administration of a gastric acid secretion inhibitor.

9. The method of treating hyperchlorhydria or excessive production of gastrin according to claim 8, wherein the subject in need thereof is a human.

10. The method of treating hyperchlorhydria or excessive production of gastrin according to claim 8, wherein the lactic acid bacterium is administered in a single dose or divided into two or more doses per day.

11. The method of treating hyperchlorhydria or excessive production of gastrin according to claim 8, wherein the lactic acid bacterium is a *Lactobacillus johnsonii* No. 1088 (accession number: NITE BP-278).

12. The method of treating hyperchlorhydria or excessive production of gastrin according to claim 11, wherein the subject in need thereof is a human.

13. The method of treating hyperchlorhydria or excessive production of gastrin according to claim 11, wherein the lactic acid bacterium is administered in a single dose or divided into two or more doses per day.

* * * * *